US009760856B2

(12) United States Patent
Chouhan et al.

(10) Patent No.: US 9,760,856 B2
(45) Date of Patent: Sep. 12, 2017

(54) INVENTORY MANAGEMENT

(71) Applicant: TATA CONSULTANCY SERVICES LIMITED, Mumbai (IN)

(72) Inventors: Himanshu Chouhan, Mumbai (IN); Murugan K, Mumbai (IN); Vijay Prakash Srinivasan, Mumbai (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 481 days.

(21) Appl. No.: 14/144,847

(22) Filed: Dec. 31, 2013

(65) Prior Publication Data
US 2015/0186836 A1 Jul. 2, 2015

(51) Int. Cl.
| | |
|---|---|
| *G06Q 10/00* | (2012.01) |
| *G06Q 30/00* | (2012.01) |
| *G06Q 50/00* | (2012.01) |
| *G06Q 10/08* | (2012.01) |
| *G06F 17/30* | (2006.01) |
| *G06F 19/00* | (2011.01) |

(52) U.S. Cl.
CPC ..... *G06Q 10/087* (2013.01); *G06F 17/30867* (2013.01); *G06F 19/3475* (2013.01); *G06F 19/327* (2013.01)

(58) Field of Classification Search
USPC .......................................................... 705/28
See application file for complete search history.

(56) References Cited

U.S. PATENT DOCUMENTS

| | | | | |
|---|---|---|---|---|
| 6,204,763 B1 * | 3/2001 | Sone | .................... | A47G 29/141 221/2 |
| 6,735,479 B2 * | 5/2004 | Fabian | ................ | A61B 5/0031 128/903 |
| 6,811,516 B1 * | 11/2004 | Dugan | ................ | G06F 19/3418 482/1 |
| 7,024,369 B1 * | 4/2006 | Brown | ................. | G06F 19/345 600/300 |

(Continued)

OTHER PUBLICATIONS

Mathaba, S, Dlodlo, N, Smith, A, Makitla, I, Sibiya, G and Adigun, M. Interfacing internet of things technologies of RFID, XMPP and Twitter to reduce inaccuracies in inventory management. IST Africa 2012, Dar es Salaam, Tanzania, May 9-11, 2012.*

(Continued)

*Primary Examiner* — Ashford S Hayles
(74) *Attorney, Agent, or Firm* — Hamre, Schumann, Mueller & Larson, P.C.

(57) ABSTRACT

The present subject matter relates to method(s) and system(s) to manage home inventory based on health of a user. The method comprises obtaining at least one health target for the user, wherein the at least one target is related to at least one health parameter. Further, querying a recipe recommender data to recommend at least one recipe based on the at least one health target. The method further comprises ascertaining the availability of one or more items to be used in the at least one recipe in a home inventory of the user, wherein the availability is ascertained based on an available stock and expiry date, and wherein the available stock of each item from among the one or more items is determined periodically, by using a core analytics engine, to manage the home inventory and health of the user.

9 Claims, 3 Drawing Sheets

(56) References Cited

U.S. PATENT DOCUMENTS

| | | | | |
|---|---|---|---|---|
| 7,065,501 B1* | 6/2006 | Brown | G06Q 10/087 | 705/22 |
| 7,979,309 B1* | 7/2011 | Stevens | G06Q 10/087 | 705/26.7 |
| 8,249,946 B2* | 8/2012 | Froseth | G06Q 10/08 | 416/72 |
| 8,321,302 B2* | 11/2012 | Bauer | G06K 7/0008 | 705/22 |
| 9,159,088 B2* | 10/2015 | Dillahunt | G06Q 30/0261 | |
| 9,412,086 B2* | 8/2016 | Morse | F25D 29/00 | |
| 2002/0027164 A1* | 3/2002 | Mault | A61B 5/1118 | 235/462.46 |
| 2003/0158796 A1* | 8/2003 | Balent | G06Q 30/0633 | 705/28 |
| 2005/0113649 A1* | 5/2005 | Bergantino | G06Q 50/22 | 600/300 |
| 2006/0074716 A1* | 4/2006 | Tilles | G06Q 30/02 | 705/2 |
| 2006/0178947 A1* | 8/2006 | Zsigmond | B07C 5/34 | 705/26.1 |
| 2009/0075242 A1* | 3/2009 | Schwarzberg | G09B 19/0092 | 434/127 |
| 2009/0099873 A1* | 4/2009 | Kurple | G06Q 50/24 | 705/3 |
| 2009/0234839 A1* | 9/2009 | Angell | G06Q 10/04 | |
| 2009/0275002 A1* | 11/2009 | Hoggle | G09B 19/0092 | 434/127 |
| 2009/0276487 A1* | 11/2009 | Jensen | G06F 19/3418 | 709/203 |
| 2010/0136508 A1* | 6/2010 | Zekhtser | G09B 19/0092 | 434/127 |
| 2010/0138203 A1* | 6/2010 | Alferness | G06F 19/3437 | 703/11 |
| 2011/0055044 A1* | 3/2011 | Wiedl | G06Q 30/02 | 705/26.5 |
| 2011/0167100 A1* | 7/2011 | Brodowski | A23L 5/10 | 708/105 |
| 2012/0016781 A1* | 1/2012 | Hashimoto | G06Q 10/087 | 705/29 |
| 2012/0059664 A1* | 3/2012 | Georgiev | A61B 5/02 | 705/2 |
| 2012/0072233 A1* | 3/2012 | Hanlon | G06F 19/3475 | 705/2 |
| 2012/0101876 A1* | 4/2012 | Turvey | G06Q 30/02 | 705/14.1 |
| 2012/0183932 A1* | 7/2012 | Chang | G09B 5/125 | 434/127 |
| 2013/0138656 A1* | 5/2013 | Wheaton | G06F 17/30705 | 707/740 |
| 2013/0218511 A1* | 8/2013 | Mager | G01G 23/3735 | 702/129 |
| 2014/0095479 A1* | 4/2014 | Chang | G06F 17/30699 | 707/722 |

OTHER PUBLICATIONS

Mathaba, S, Dlodlo, N, Smith, A, Makitla, I, Sibiya, G and Adigun, M. Interfacing internet of things technologies of RFID, XMPP and Twitter to reduce inaccuracies in inventory management. 1ST Africa 2012, Dar es Salaam, Tanzania, May 9-11, 2012.*

"MealEasy Professional Software Now Offers Dietitians, Nutritionists and Health Coaches Client Support to Aid Weight Loss and Create Customized Nutritional Meal Plans", Noviden Technologies Inc., Jun. 25, 2013, 2 pages. http://www.prweb.com/releases/2013/6/prweb10841320.htm.

"Nest Egg—Inventory 3.8 for iOS: Home Inventory Management with Alerts", Winprogger, LLC, Aug. 6, 2012, 3 pages. http://prmac.com/release-id-46236.htm.

* cited by examiner

INVENTORY MANAGEMENT

TECHNICAL FIELD

The present subject matter relates, in general, relates to inventory management and in particular, relates to home inventory management.

BACKGROUND

The residents of a home regularly purchase a variety of items for use and consumption in the household. Such purchased items include groceries and other supplies, such as trash bags, cleaning supplies, and toiletries. The purchase is typically done by a member of the household by shopping in a store, such as a grocery store, or via on-line shopping. The purchased items are typically stored in various storage areas inside the residence, such as a refrigerator, freezer, cabinets or pantry. As and when certain items in the home inventory get depleted, those items have to be replenished. The current stock of items constitutes the home inventory of such items. Generally, an optimal stock of items is to be maintained in the household so that the items are available when required and at the same time it is ensured that unnecessary stock does not get piled up. Suitable measures taken towards maintaining the optimal stock of items of each item in the home inventory is referred to as home inventory management.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

Figure 1A:
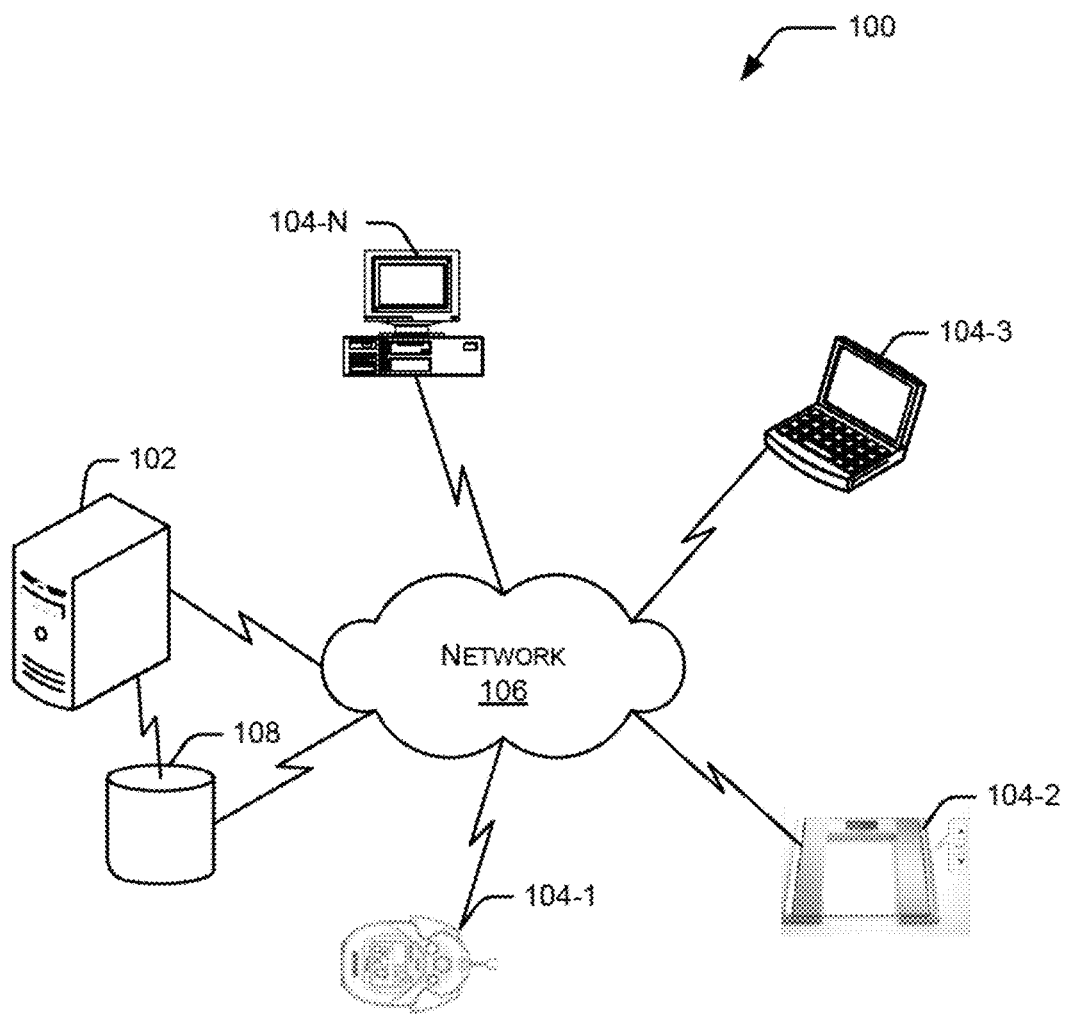
FIG. 1a illustrates a network environment implementing an inventory management system, in accordance with an embodiment of the present subject matter.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

DETAILED DESCRIPTION

Methods and systems for inventory management for a user are described. The inventory management systems of the present subject matter are provided to the user, by a service provider, such as a retailer, for efficient management of home inventory and health requirements of the user. Although the description herein refers to the service provider facilitated inventory management system, it may be understood that the inventory management system may be implemented by the user as standalone system. In an example, the user may be a person or a family of persons at home implementing the inventory management system for managing the home inventory and health requirements.

Conventionally, for home inventory management, the user may generate a shopping list indicating a list of items that need to be purchased or replenished based on an estimate of stock of each item in the home inventory. However, at times, the user may fail to keep a right track of stock of each item in the home inventory. As a result, the user may, at times, end up purchasing items that are already available in the home inventory, thereby leading to wastage of the item. In certain other cases, upon returning home from the store, the user may realize that he had forgotten to purchase one or more required items. For example, a user may wish to cook dinner using a recipe that requires cheese, but the user may discover that no cheese is present in the home inventory, or that the available cheese has expired. Thus, the user must abandon the desired meal and switch to a less-desirable substitute. In such cases, the user may be burdened to make a visit to the grocery store again, to purchase the required items.

Also, with so many new items being developed and placed in the market for users' purchase the service providers, such as retailers, are often tasked with managing the inventory of store. In addition, in conventional methods, the service provider is often uncertain about the consumption pattern of an item and hence finds it difficult to determine an optimal stock level that is to be maintained in the store. In such a scenario, if the service provider selling finished goods has an insufficient on-hand inventory; sales may be lost when the users go elsewhere to purchase the unavailable goods. Alternatively, maintaining an excess of on-hand inventory may increase costs for the service provider.

Further, in conventional methods, users' have to spend valuable time making shopping lists, grocery shopping and planning meals, to manage one's diet and health. Several sources including news articles, magazines, books, television, and internet provide suggestions to maintain a healthy lifestyle by providing general health and diet information, such as healthy food choices and recipes, nutritional statistics, exercise routines, and required calorie intake to the user. Such conventional methods are very generic and are not tailored to the health conditions, or health goals of a particular user.

Present subject matter provides system based approach for enabling the users to manage their home inventory and health requirements, by implementing the described methods. The described methods and systems provide an efficient solution for managing the home inventory for the user, by Obviating the need for manual intervention, thereby easing the process of the inventory management. Such management of the home inventory is based on periodic determination of the stock level, by learning the consumption pattern of the user, for each item in the home inventory. Therefore, if the stock of an item is low, the described systems may notify the user ahead of time to enable the user to place an order and replenish the item before the item runs out of stock, thereby easing the process of home inventory management.

Further, the system can proactively recommend recipes to the user based on the health of the user. Such a recommendation takes into consideration the health information, health targets, of the user; and is therefore highly personalized to the user. Further, the system can also manage inventory and provide purchase suggestions based on the recommended recipes. Thus the inventory can be managed also based on the health requirements of the user.

In operation, in one implementation, one or more inventory inputs corresponding to a purchase may be obtained and the inputs associated with the purchase are stored in a home inventory data. Since the system of the present subject matter is provided to the user by the service provider, the service provider may have access to user's account details, and the inventory inputs may be obtained, for example, based on the billing. Hence this system can be integrated/receive inputs from the service provider's billing/purchase system. In another example, if the inventory management system is implemented as a standalone system, the inventory inputs may be obtained by the system, from the user. In both the examples as described above, the inventory inputs may be one or more of an item name, quantity, location of purchase, serial number, expiry date, and price. In an example, the inventory inputs may be obtained by reading a tag, such as Radio Frequency Identification (RFD) tag, associated with each item. The tag may contain information about the item such as quantity, location of purchase, serial number, price expiry date of the item serial number, a date, and any other attribute associated with the item. Accordingly, when a reader reads a tag, the inventory inputs can be obtained about the associated item that hosts the tag.

In another example, the inventory inputs may be obtained by scanning a barcode associated with an item. The scanner may further decode the information associated with the barcode, such as the quantity, location of purchase, serial number, price, and expiry date of the item, and store the decoded information in the home inventory data. In another example, the inventory inputs may be obtained through a voice recognition tool, so that the user can input the item information by speaking the describing the item. In another implementation, the inventory inputs corresponding to an item may be obtained by allowing the user to manually enter the information corresponding to each item.

Further, each of the items in the home inventory data is categorized into categories. The categories may correspond to purpose or use of an article. In an example, the categories may include grocery, office supplies, white goods, home appliances, garden supplies, wardrobe supplies, and toiletries. Such a categorization of each item in the home inventory data may be performed based on pre-defined rules to categorize each of the purchased item to the listed categories. For example, consider a user has purchased a list of items comprising frozen vegetables, bread, milk, eggs, shampoo, and stationary. In such an instance, the frozen vegetables, bread, milk, eggs may be categorized under the grocery section, shampoo may be categorized under the toiletries section and books may be categorized under the office supplies, accordingly. The categorization of each item in the home inventory data into one of the listed categories is based on purpose of the item. In another example, the system may allow the user to categorize each of the items into one of the categories.

In another example, the items in the home inventory data may be further categorized depending on a calculation between the acquired date and the expiration date of the item. Such categorization is to keep a track of the freshness of each item, where the freshness is indicative of whether the item is fresh, about to expire or expired. The items that have a long shelf life, the, "fresh" category. Similarly, certain other items are only "fresh" for a limited time. Therefore, such items may be categorized under the, "about to expire" category. Similarly, certain other items, such as milk and cheese have a very short shelf life period before they get spoilt. Therefore, in situations Where the items have exceeded the expiry date, they may be categorized under the, "expired" category. This calculation is performed at pre-defined time intervals, such as daily or weekly, to determine in which category the items should be listed; and the corresponding information is updated in the home inventory data periodically. Such categorization may be performed by decoding the information associated with the tag, where the tag contains information regarding the expiry date of each item. Such categorization may help alert the user when the item has expired or when the item is about to expire to enable the user consume the item before the expiry date, thereby reducing wastage. In an example, where the item is not pre-tagged with an expiry date, the system may allow the user to manually enter the inventory inputs corresponding to the expiry date, for each item.

Further, the available stock is determined periodically for each item in the home inventory. The available stock is the quantity of an item that is available for use. Further, the period of time for which the available stock may last is determined based on the rate of consumption and the available stock of each item in the home inventory. In an implementation, the available stock is determined by using a core analytics engine leverages Internet of Things (IOT) to determine a weight associated with each item in the home inventory. The IoT combines different information sensing devices, such as radio frequency identifications (RFID), sensors, and computing devices with internet to determine the weight of each item periodically, where the weight is indicative of the available stock.

Further, the core analytics engine may allow the user to place an order by generating a list of items that need to be replenished based on available stock. In addition to generating the list of items, the core analytics engine may also determine the optimal stock that need to be ordered while generating the list of items for replenishment. The determination is based on learning one or more of a frequency of purchase of an item, consumption pattern of the item, and the expiry date of the item. Therefore, the core analytics engine may determine if the user has to place an order for 1 liter of milk or 500 ml of milk based on the learning of the historical consumption and purchase patterns. Once the list is generated, the user may place an order requesting for delivery of goods or items from the service provider using the inventory management system. This may save a substantial amount of time for the user, as the user may no longer have to keep a manual track of stock of each item in the home inventory. Also since the system is capable of determining the optimum stock that need to be ordered, over stocking can be avoided and hence there may be a substantial reduction in the wastage of items.

In addition to providing an efficient method to manage the home inventory, the system implementing the described methods can also monitor the health of the user based on the home inventory and suggest purchases to assist the user meet predefined health goals. The health of the user can be monitored by aggregating inputs on health parameters, such as body weight, body mass index (BMI), glucose level, blood pressure levels, and heart rate. In an example, the health inputs may be obtained by communicating with online health portals and/or medical devices, such as weighing scales, thermometers, pedometers, blood pressure monitors, and health bands. Such seamless communication among the medical devices and the inventory management system, to share the inputs associated with the health parameters over a communication network, can be implemented based on Internet of Things (IoT). Further, such an application allows for effective health monitoring of users whose physiological status requires close attention. In yet another example, the user may be manually allowed to enter health inputs corresponding to the health parameters.

Further, the health targets for the one or more health parameters are determined based on the health inputs. In an example, the user may manually enter the one or more health targets by comparing the health inputs with pre-defined values, for the one or more health parameters. Further, the health inputs that deviate from the pre-defined values suggest the need for monitoring the particular health parameter. For example, a substantial deviation in the blood glucose levels from the pre-defined value indicates the need for monitoring the blood glucose levels. Therefore, the user can utilize this information to set health targets for the one or more health parameters, food habits, or other parameters based on preferences of the user.

Furthermore, the system may recommend recipes based on the one or more health targets. Such recommendation of the recipes is to enable the user achieve the set health targets. In an example, the recipes may be recommended by the system by querying a recipe recommender data to generate recipes based on one or more of the health targets and choice of the user. The recipe recommender data includes a variety of pre-set healthy recipes to assist the user in preparing a meal based on the health targets. The generated recipes are stored in the recipe recommender data. Further, upon recommending recipes, the system may ascertain if the one or more items for the recommended recipe are available in the home inventory data. If the items for the recommended recipe are available in the home inventory data, the user may prepare a meal by consuming the one or more items and the available stock of the consumed items is determined accordingly.

In a scenario, where the one or more items for the recommended recipe are unavailable in the home inventory data, the system may notify the one or more items that are available to enable the user place an order for the same. Further, once the user places the order, the request is processed and is notified to the service provider, such as the retailer or a warehouse. Depending on the type of order, i.e., if it is for home delivery or pick up at store, the purchased items are either delivered at home or sent to the specified store. After the delivery or pick up of the item the home inventory data is updated.

The described methods and the systems of the present subject matter provide for managing the home inventory of the user and also manage a health profile of the user with the home inventory. Since the inventory management system of the present subject matter is provided by the service provider, he is aware of the user's home inventory and purchase pattern, and is therefore efficiently able to manage the home inventory for the user, thereby saving a substantial amount of time to the user. Also, the service provide is able to effectively manage his inventory based on the understanding purchase pattern of the user. Further, since the service provider is able to effectively up sell and cross sell the items, and is therefore able to effectively market new items and sell his merchandise.

Also, the systems of the present subject matter may enable the user to place an order of optimal stock, as determined based on learning the historical consumption and purchase pattern of the user. Such determination may save a substantial amount of time for the user, as the user may no longer have to keep a manual track of stock of each item in the home inventory. Also since the system is capable of determining the optimum stock that need to be ordered, over stocking can be avoided and hence there may be a substantial reduction in the wastage of items.

Further, the systems of the present subject matter allows for effective monitoring of health by utilizing Internet of things (IoT) for seamless communication among the medical devices to obtain health information and health targets of the user. Such methods are particularly effective for physiological monitoring of patients suffering from a particular health condition. Since, the described methods take into consideration the health information, and health targets of the user, the recipes recommended to user are highly personalized to the user and assist the user to achieve the health targets. Such recommendation of the recipes saves a substantial amount of time for the user, thereby easing the entire process of meal preparation. The present subject matter also allows for notifying the user of the items unavailable in the home inventory data for a recommended recipe and enables the user place an online order, thereby easing the process of grocery shopping.

Figure 1B:
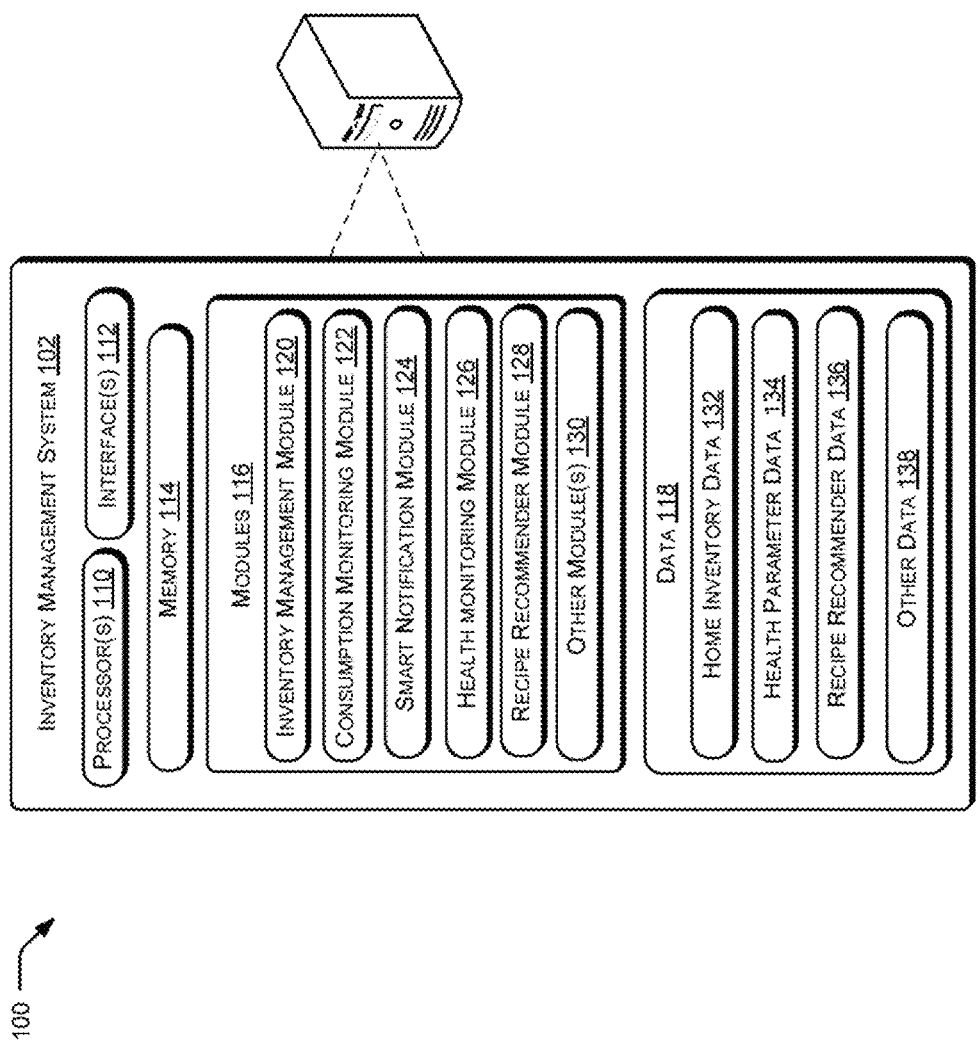
FIG. 1b illustrates components of the inventory management system, in accordance with an embodiment of the present subject matter.
Figure 2:
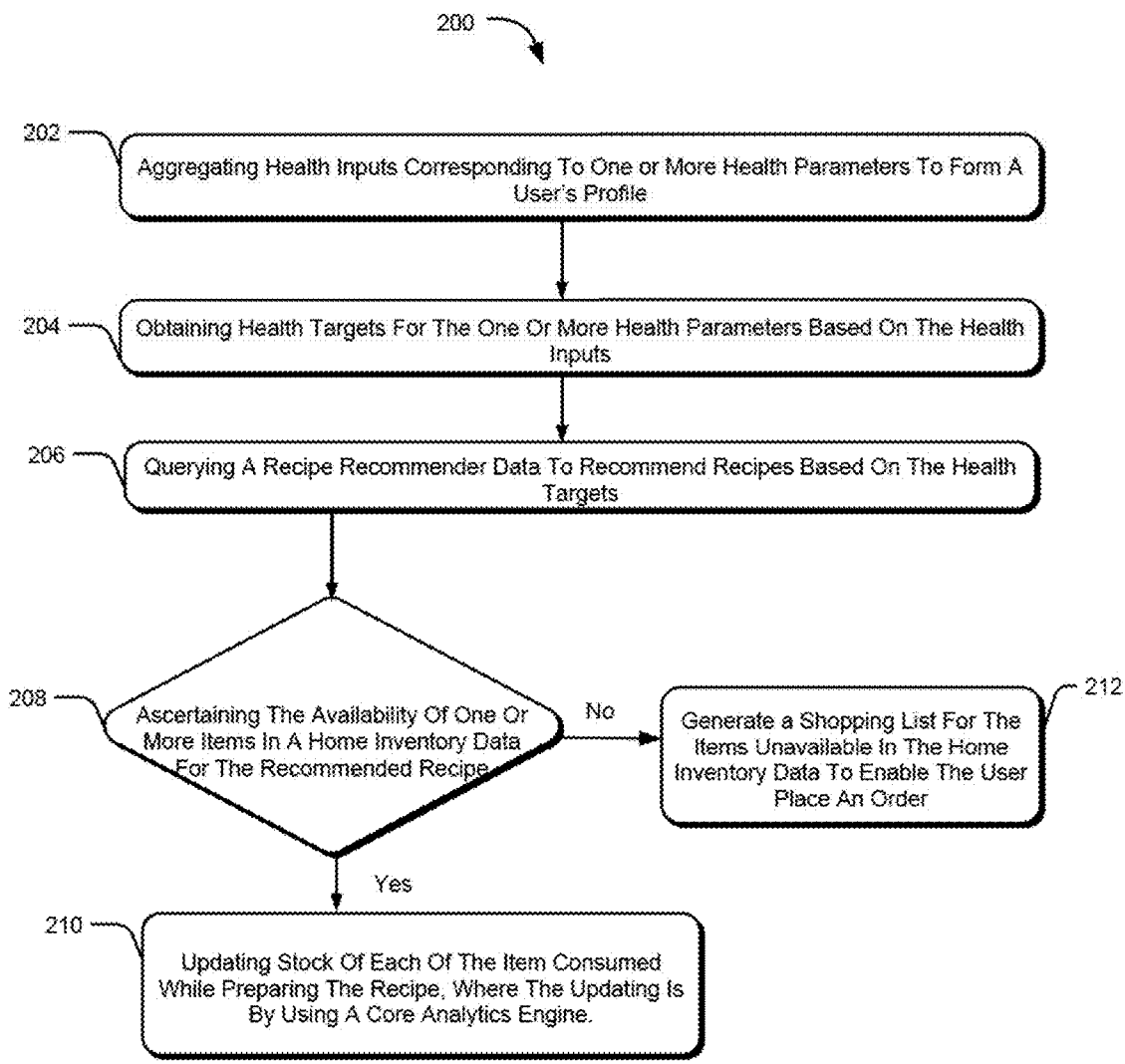
FIG. 2 illustrates a method for inventory management based on health of the user, in accordance with an embodiment of the present subject matter.

The manner in which the systems and methods shall be implemented has been explained in details with respect to FIGS. 1a, 1b, and 2. Methods can be implemented in systems that include, but are not limited to, desktop computers, hand-held devices, laptops or other portable computers, and the like. Although the description herein is with reference to computing devices, the methods and systems may be implemented in other devices and systems as well, albeit with a few variations, as will be understood by a person skilled in the art. While aspects of described systems and methods can be implemented in any number of different computing devices, transmission environments, and/or configurations, the implementations are described in the context of the following system(s).

FIG. 1a illustrates a network environment 100 implementing inventory management systems 102, to manage home inventory based on health targets of a user, the method, in accordance with an embodiment of the present subject matter. The inventory management system 102 may be simply referred to as the system 102, herein after. The system 102 described herein, can be implemented in a variety of network devices, including, computing devices, medical devices, storage devices, etc. In one implementation the system 102 is connected to one or more user devices 104 through a network 106. The user devices 104-1, 104-2, ... 104-N may include multiple applications that may be running to perform several functions. The system 102 can be implemented as a computing device, such as a smart phone, tablet, laptop computer, a desktop computer, a notebook, a workstation, a mainframe computer, desktop computers, hand-held devices, laptops or other portable computers, tablet computers, mobile phones, PDAs, Smartphones, and the like.

In one implementation, the system 102 facilitates management of home inventory based on health targets of a user. In an example, the system 102 may be connected with the order management system of a service provider over the network 106. The network 106 may be a wireless or a wired network, or a combination thereof. The network 106 can be a collection of individual networks, interconnected with each other and functioning as a single large network (e.g., the internet or an intranet). Examples of such individual networks include, but are not limited to, Global System for Mobile Communication (GSM) network, Universal Mobile Telecommunications System (UMTS) network, LTE 4G networks, Personal Communications Service (PCS) network, Time Division Multiple Access (TDMA) network, Code Division Multiple Access (CDMA) network, Next Generation Network (NGN), Public Switched Telephone Network (PSTN), and Integrated Services Digital Network (ISDN). Depending on the technology, the network 106 includes various network entities, such as gateways, routers, however, such details have been omitted for ease of understanding.

The network environment 100 further comprises a database 108 coupled with the system 102. The system 102 may obtain data from the database 108 to manage the home inventory and health of the user. Although the database 108 is shown external to system 102, it will be appreciated by a person skilled in the art that the database 108 can also be implemented internal to the system 102. Further the database 108 can be a single database or a collection of databases, such as a data warehouse or distributed databases maintained by different entities. For example, there can be a purchase items database maintained by a service provider and a health parameter database maintained by a healthcare services agency.

Further, the manner in which the home inventory is managed based on the health targets of the user by different components of the system 102 is described in detail with reference to the FIG. 1b. FIG. 1b illustrates components of the system 102, in accordance with an embodiment of the present subject matter. In an implementation, the system 102 includes processor(s) 110. The processor(s) 110 may be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory.

The system 102 also includes interface(s) 112. The interface(s) 112 may include a variety of machine readable instruction-based and hardware-based interfaces that allow the system 102 to interact with other systems and devices, including servers, data sources, and external repositories. Further, the interface(s) 112 may enable the system 102 to communicate with other communication devices, such as network entities, over a communication network.

Further, the system 102 includes a memory 114. The memory 114 may be coupled to the processor(s) 110. The memory 114 can include any computer-readable medium known in the art including, for example, volatile memory, such as static random access memory (SRAM) and dynamic random access memory (DRAM), and/or non-volatile memory, such as read only memory (ROM), erasable programmable ROM, SSDs flash memories, hard disks, optical disks, and magnetic tapes.

Further, the system 102 includes module(s) 116 and data 118. The module(s) 116 and the data 118 may be coupled to the processor(s) 110. The modules 116, amongst other things, include routines, programs, objects, components, data structures, etc., which perform particular tasks or implement particular abstract data types. The modules 116 may also be implemented as, signal processor(s), state machine(s), logic circuitries, and/or any other device or component that manipulate signals based on operational instructions. The data 118 serves, amongst other things, as a repository for storing data that may be fetched, processed, received, or generated by the module(s) 116. Although the data 118 is shown internal to the device 102, it may be understood that the data 118 can reside in an external repository (not shown in the figure), which may be coupled to the system 102. The system 102 may communicate with the external repository through the interface(s) 106.

Further, the module(s) 116 can be implemented in hardware, instructions executed by a processing unit, or by a combination thereof. The processing unit can comprise a computer, a processor, a state machine, a logic array or any other suitable devices capable of processing instructions. The processing unit can be a general-purpose processor which executes instructions to cause the general-purpose processor to perform the required tasks or, the processing unit can be dedicated to perform the required functions. In another aspect of the present subject matter, the module(s) 116 may be machine-readable instructions (software) which, when executed by a processor/processing unit, perform any of the described functionalities. The machine-readable instructions may be stored on an electronic memory device, hard disk, optical disk or other machine-readable storage medium or non-transitory medium. In one implementation, the machine-readable instructions can be also be downloaded to the storage medium via a network connection.

In an implementation, the module(s) 116 include an inventory management module 120, a consumption monitoring module 122, a smart notification module 124, a health monitoring module 126, a recipe recommender module 128, and other module 130. The other module(s) 130 may include programs or coded instructions that supplement applications or functions performed by the system 102. In said implementation, the data 118 includes home inventory data 132, health parameter data 134, a recipe recommender data 136, and other data 140. The other data 140 amongst other things, may serve as a repository for storing data that is processed, received, or generated as a result of the execution of one or more modules in the module(s) 116.

As mentioned above, the system 102 provides for managing the home inventory and manage health profile of the user along with the home inventory. Since the system 102 of the present subject matter is provided to the user by the service provider, the service provider may have access to user's account details, where he may provide the inventory inputs associated with the purchase. In one implementation, the service provider can provide an Application that can be downloaded and installed by the user on any communication device, and such communication device with the Application installed on it will be able to operate as the system 102. In another implementation, a specific communication device with networking capabilities may be provided to the user. In another example, system 102 may be presented to the user by multiple service providers to manage the home inventory. For example, the system 102 may be provided by Walgreens, Wal-Mart and Home Depot. In another example, if the 102 system is implemented as a standalone system, the inventory inputs may be obtained by the system 102, from the user end. In both the examples as described above, the inventory management module 120 may obtain inventory inputs corresponding to a purchase and store the obtained inventory inputs in a home inventory data 132.

Further, the purchase may correspond to a new item or may correspond to replenishment of an existing item. If the purchase corresponds to a new item, the inventory management module 120 may add each of the new item and the inventory inputs associated with the new item in the home inventory data 132. However, if the purchase corresponds to replenishment of an existing stock, the inventory management module 120 may update the inventory inputs associated with the item and store the updated inventory inputs in the home inventory data 132.

Further, the inventory inputs include one or more of a brand name, quantity, location of purchase, serial number, expiry date, and price. In an example, the inventory inputs may be obtained by reading a tag. In an example, the inventory inputs may be obtained based on Internet of Things (IoT). The IoT is an emerging technology, combining different information sensing devices, such as radio frequency identifications (RFID), sensors, laser scanners, with internet to form a huge network. In another example, the inputs may be obtained by a Radio Frequency Identification (RFID) tag, associated with each item. The tag may contain information about the item, such as quantity, location of purchase, serial number, price expiry date of the item serial number, a date, and any other attribute associated with the item. Accordingly, when a reader reads a tag, such as the RFID tag, the information associated with the tag may be decoded to obtain the inventory inputs associated with the item that hosts the tag. The inventory inputs are further stored in the home inventory data 132.

In another example, the inventory inputs may be obtained by scanning a barcode associated with an item. Each item may be associated with a unique barcode and the scanner may further decode the information associated with the barcode, such as the quantity, location of purchase, serial number, price, and expiry date of the item. The inventory inputs are further stored in the home inventory data 132.

In another example, the inventory inputs may be obtained through a voice recognition tool, so that the user can input the item information by speaking the describing the item. For example, the user may describe the information associated with the item, such as "apple" and then describe the quantity and other information associated with the item. In another implementation, the inventory inputs corresponding to an item may be obtained by allowing the user to manually enter the information corresponding to each item.

Further, the inventory management module 120 may categorize each item into categories based on the inputs. The categories correspond to purpose or use of an item. The categories may include one or more of a grocery, office supplies, white goods, home appliances, garden supplies, wardrobe supplies, and toiletries. Such a categorization of each item in the home inventory data 132 may be performed based on pre-defined rules to categorize each of the purchased item to the listed categories. For instance, if a user has purchased items, such as books, shampoo, hangers, tube lights, frozen vegetables and milk, the inventory management module 120 may categorize each of the items into one of the categories as listed based on the purpose. Therefore, frozen vegetables and milk may be categorized under grocery, shampoo may be listed under toiletries, books may be listed under office supplies, etc. In another example, the inventory management module 120 may offer flexibility to the user to categorize each of the items in the home inventory data 132 to one of the categories.

In another example, the inventory management module 120 may categorize each item based on the inputs, such as the expiry date. Such categorization is to determine the freshness of each item in the home inventory data 132, where the freshness is indicative of whether the item is fresh, about to expire or expired. The items in the "fresh" are fresh and not near the expiration date. The items in the "about to be expired" category are to be used within a pre-determined time period, and these items are close to their expiration date and will soon pass their expiration date if not used within the pre-determined time period. The predetermined time period can be a pre-set time by the system or can be defined by the user. The items in the "expired" category have reached or are past their expiration date.

Accordingly, the inventory management module 120 may categorize the one or more items to the listed categories, depending on a calculation between the acquired date and the expiration date of the item. For example, consider a user has purchased a list of items comprising potatoes, frozen vegetables, bread, and milk. Upon obtaining inputs on the expiry date, the inventory management module 120 may categorize each of these items to one of a fresh, about to expire or expired category. Therefore, frozen vegetables, bread, and milk, which have a short expiry date, may be categorized into "about to expire" category as they need to be consumed by the user in a short time frame. Further, the potatoes may be categorized under the, "fresh" category, since they have a long shelf life. This calculation is performed at pre-defined time intervals, such as daily, to determine in which category the items should be listed. Such categorization may be performed by decoding the information associated with the tag, where the tag contains information regarding the expiry date of each item. Further, a reader suitable to scan the RFID tag may decode the information associated with the tag. Since the calculation is performed at pre-defined intervals, the corresponding tag is updated periodically. Such tagging may alert the user when the item has expired or when the item is about to expire to enable the user consume the item before the expiry date, thereby reducing wastage of the item. In an example, where the item is not pre-tagged, the user may manually enter the expiry date corresponding to each item. Further, each of the categories based on the inventory inputs are stored in the home inventory data 132.

Further, the system 102 may keep a track of available stock of each item in the home inventory data 132. For this purpose, the consumption monitoring module 122 may determine the available stock of each item in the home inventory data 132 at periodic intervals. The available stock is the quantity of an item that is available for use. In an example, a weight of an item in the home inventory can be considered as the available stock, such as 10 pounds of rice. In another example, the number of available units is indicative of available stock, such as 20 candies. Further, the period of time for which the available stock may be available is determined based on the rate of consumption and the available stock of each item in the home inventory data 132. For instance, consider a stock of 20 pounds of rice in home inventory. If the rate of consumption of rice is 1 pound per day, the time period for which the rice may be available is 20 days. In an example, such determination of the available stock is by using a core analytics engine leverages the concept of Internet of Things (IoT) to determine a weight associated with each item in the home inventory. In said example, the weight is indicative of the available stock.

Further, the core analytics engine of the consumption monitoring module 122 may determine the items that need to be replenished based on available stock. In addition, the core analytics engine may also determine the optimal stock that need to be ordered while determining the list of items for replenishment and store the information associated with the stock levels in the home inventory data 132. The optimal stock is the average quantity required to provide a given fill rate. This may differ from item to item in the home inventory. For instance, maintaining a stock level of 1 liter of milk for a family of two may be an optimal stock, as opposed to maintaining 10 liters of milk. Such determination is based on learning one or more of a frequency of purchase of an item, consumption pattern of the item, and the expiry date of the item. For example, dairy products, such as milk, have a short shelf life and are likely to get spoilt soon. Hence, it is preferable that such items are purchased more frequently rather than maintaining a over stock at home. Therefore, for a user consuming 1 liter of milk a day, the core analytics engine may determine the optimal stock of milk that may be maintained at the user's home to be 2 to 3 liters, while generating the list of items for replenishment. Such determination may save a substantial amount of time for the user, as the user may no longer have to keep a manual track of stock of each item in the home inventory. Also since the system is capable of determining the optimum stock that need to be ordered, over stocking can be avoided and hence there may be a substantial reduction in the wastage of items.

Further, upon determination of the optimal stock, the smart notification module 124 of the system 102 may notify the user of the stock of the items that need replenishment. The user can utilize this information, to automatically generate shopping lists, manage home inventory, plan meals based on items available in the home inventory, and schedule activity to enable the user to plan shopping of required items. In another example, the smart monitoring module 124 may make a purchase based on the learning performed by the consumption monitoring module 122.

Further, the smart notification module 124 may keep a track of favorite shopping lists for each user. Such a list is determined based on learning the historical purchase pattern of items. Therefore, if a user has been regularly purchasing a dozen eggs over every alternate week, the smart notification module 124 may add eggs to the user's favorite shopping list. Since the items that are purchased regularly are added to the favorite shopping lists, the smart notification module 124 may place an order on a scheduled date for the items listed in the favorite shopping list, thereby circumventing the need for manual intervention.

The smart notification module 124 may also offer discounts and coupons to users who have made a purchase beyond a pre-defined amount. For example, consider a user who has been a regular customer for a particular service provider, making a purchase for 1000 USD. In such cases, the smart notification module 124 may offer certain discounts or provide coupons, if the purchase has exceeded the pre-defined amount. Such an option may increase the customer loyalty and strengthen the relationship between the service provider and the user.

Further, the smart notification module 124 may provide alerts and preferences to the user. In an example, the alerts and preferences may be notified based on understanding the user's purchase pattern. Therefore, if a user has been regularly purchasing varied cosmetics, the smart notification module 124 may alert the user of new cosmetics that have been launched in the market. Such knowledge of user's purchase patterns may enable the service provider to effectively up sell and cross sell the items and merchandise available with him.

Further, the smart notification module 124 may determine the burn rate for the user. This may enable the user to keep a track of finances spent towards the home inventory. Further, the smart notification module 124 may also maintain the user's personal information and login information. The personal information may include demographic data and geographical location of the user to enable the service provider deliver goods to the user upon placement of an order. Further, since the system 102 of the present subject matter is provided to the user by the service provider, the service provider is now aware of available stock, purchase pattern, geographical location of the user. Further, the service provider may also understand the available stock and purchase pattern of several of its users implementing the system 102, in order to determine an optimal stock that is to be maintained at the service provider end, for efficient management of the user's home inventory.

In addition to providing an efficient method to manage the home inventory, the system 102 also correlates the health profile of the user based on the home inventory. For this purpose, the health monitoring module 126 may aggregate health inputs corresponding to one or more health parameters to determine if the user suffers from any medical conditions or ailments, such as high cholesterol, diabetes, high blood pressure, arthritis, migraines, or food allergies. The health parameters may include one or more of body weight, body mass index (BMI), glucose level, blood pressure levels and heart rate, etc.

In an example, the health monitoring module 126 may obtain the health inputs by communicating with medical devices 104-1 and 104-2 and online health portals over the network 106. The medical devices 104-1 and 104-2 may include wearable computing devices, health monitors, weighing scales, health bands, pedometers, thermometers, and heart rate monitors. For instance, the weighing scales, recording the weight and height of the user, may communicate with the health monitoring module 126 over the network 106. The health monitoring module 120 may further determine the BMI based on the health inputs corresponding to the height and weight. Such seamless communication among the medical devices 104 and the system 102 to share the health inputs associated with the health parameters over a network 106, is based on Internet of Things (IoT). Further, such an application allows for effective health monitoring of patients whose physiological status requires close attention.

In another example, the health monitoring module 126 may allow the user to manually enter health inputs corresponding to the one or more health parameters.

In yet another example, the health monitoring module 126 may provide the user with a questionnaire that gathers information concerning the user's health. The questionnaire may contain information corresponding to one or more of past medical histories, surgical histories, family histories, histories of present illnesses, current and past medications, allergies and symptoms.

Further, the health monitoring module 126 may allow the user to set one or more health targets for the one or more health parameters based on the health inputs. In an example, the health targets may be set by comparing the health inputs with pre-defined values for the same health parameter. For instance, if the pre-prandial blood glucose level of a non-diabetic user is 7 mmol/L, the health monitoring module 126 may allow the user to set the health target to 6 mmol/L based on the pre-defined values available in the health parameter data 134. The health targets thus set by the user for the one or more health parameters are stored in the health parameter data 134.

Further, in order to enable the user achieve the health targets, the recipe recommender module 128 may recommend recipes to the user by referring to the health targets stored in the health parameter data 134. For example, the recipe recommender module 128 may recommend a recipe rich in proteins for an athlete trying to build muscle. Similarly, the recipe recommender module 128 may recommend a recipe that contains low sugars for a diabetic person. Such recommendation of the recipes is to enable the user achieve the set health targets.

In an implementation, recipes are recommended by the recipe recommender module 128 querying a recipe recommender data 136 to generate recipes based on one or more of the health targets and choice of the user. The recipe recommender data 136 includes a variety of pre-set healthy recipes to assist the user in preparing a meal based on the health targets. In an example, the recipe recommender module 128 may further take into consideration at least one of the stock level or expiration dates for the items that are available in the home inventory data 132 while recommending recipes based on the health targets. Therefore, the recipes generated are based on the items available in the home inventory data 132. Also, while recommending the recipe, the items with shorter expiration period are selected before the items with longer expiration periods, while recommending a recipe. This preferential selection enables efficient meal planning and reduces wastage of items. Furthermore, the user may have consumed one or more items in the home inventory data 132 while preparing the recipe and the available stock of each of the consumed items may have decreased. Such a change in the stock level is updated accordingly by the consumption monitoring module 122. In yet another example, the recipe recommender module 128 recommend recipes without taking into consideration the items that are available in the home inventory data 132. In such a scenario, the recommended recipe may contain one or more items that may not be available in the home inventory data 132. In such a case, the consumption monitoring module 122 may determine the one or more items that are unavailable for the recommended recipe the home inventory data 132. The unavailable items include the items that have gone past the expiry date or that they are not available in the home inventory data 132 or include items that do not have an optimum stock to prepare a recipe with the available stock. In such cases, the consumption monitoring module 122 may determine the list of items for purchase and the optimal stock required for purchase of the unavailable items. Further, the smart notification module 124 may notify the list to the user, to enable the user place an order. Further, once the order is placed, the request is processed and is notified to an order management system of the service provider, such as the retailer or a warehouse. Depending on the type of order, i.e., if it is for home delivery or pick up at store, the purchased items are either delivered at home or sent to the specified store. After the delivery or pick up of the item the home inventory data 132 is updated.

The described methods and systems of the present subject matter provide managing the home inventory of the user and also correlate a health profile of the user with the home inventory. Since the inventory management systems of the present subject matter is provided by the service provider, he is aware of the user's home inventory and purchase pattern, and is therefore efficiently able to manage the home inventory for the user, thereby saving a substantial amount of time to the user. Further, since the service provider is able to effectively up sell and cross sell the items, and is therefore able to effectively market new items and sell his merchandise.

Also, the systems of the present subject matter may enable the user to place an order of optimal stock, as determined based on learning the historical consumption and purchase pattern of the user. Such determination may save a substantial amount of time for the user, as the user may no longer have to keep a manual track of stock of each item in the home inventory; and also reduce wastage of items by preventing the over stock. Further, the systems of the present subject matter allows for effective monitoring of health by utilizing IoT for seamless communication among the medical devices to obtain health information and health targets of the user. Such methods are particularly effective for physiological monitoring of patients suffering from a particular health condition.

FIG. 2 illustrates a method 200 for inventory management based on the health information and home inventory of a user. The order in which the method 200 is described is not intended to be construed as a limitation, and any number of the described method blocks can be combined in any order to implement the method 200, or any alternative methods. Additionally, individual blocks may be deleted from the method 200 without departing from the spirit and scope of the subject matter described herein. Furthermore, the method 200 can be implemented in any suitable hardware platform(s).

The method 200 may be described in the general context of computer executable instructions. Generally, computer executable instructions can include routines, programs, objects, components, data structures, procedures, modules, functions, etc., that perform particular functions or implement particular abstract data types. The method 200 may also be practiced in a distributed computing environment where functions are performed by remote processing devices that are linked through a communications network. In a distributed computing environment, computer executable instructions may be located in both local and remote computer storage media, including memory storage devices.

Further, although the method 200 may be implemented in any computing device; in an example described in FIG. 2, the method 200 is explained in context of the aforementioned device 202, for the ease of explanation.

Accordingly, referring to FIG. 2, at block 202, the health inputs corresponding to a plurality of health parameters may be obtained, to form a user profile. The health parameters may include one or more of body weight, body mass index (BMI), glucose level, blood pressure levels, cholesterol levels and heart rate. In an example, the health inputs may be obtained by communicating with medical devices in a network environment. The medical devices may include health bands, weighing scales, health portals, etc. Such seamless communication among the medical devices 104 and the system 102 to share the health inputs associated with the health parameters over a network 106, is based on Internet of Things (IoT). In another example, the health inputs may be obtained by allowing the user to manually enter health inputs corresponding to the one or more health parameters. In both the examples, as described, the health monitoring module 122 may obtain health inputs to determine the health condition of the user.

At block 204, health targets for the at least one health parameter may be obtained based on the inputs. In example, the health targets may be obtained by allowing the user to manually enter health targets corresponding to one or more health parameters by comparing the inputs corresponding to a health parameter with pre-defined values corresponding to the same health parameter. The health targets are stored in the health parameter data 134

At block 206, recipes are recommended to the user to enable the user meet the set up health targets stored in the health parameter data 134. For example, the system may recommend a recipe rich in proteins for an athlete trying to build muscle. In an implementation, recipes are recommended by querying a recipe recommender data 136 to generate recipes based on one or more of the health targets and choice of the user. The recipe recommender data 136 includes a variety of pre-set healthy recipes to assist the user in preparing a meal based on the health targets. In another example, the system may offer the flexibility to allow the user to choose a recipe from the recipe recommender data 136 suiting to the food preferences, eating habits and health targets of the user.

At block 208, the system may ascertain the availability of one or more items in the home inventory data 132 for the recommended recipe. The available stock and the expiry date for each of the items required to prepare the recommended recipe is taken into consideration while determining the availability of items in the home inventory data 132. If the items are available (Yes) in the home inventory data 132 for the recommended recipe, the method branches to block 210. Otherwise, the method branches to block 212.

At block 210, the stock of the one or more items consumed for the recommended recipe is updated in the home inventory data 132. In an example, the stock is updated based on learning the consumption pattern of each item, frequency of purchase, and the expiry date for each item in the home inventory data 132 by a core analytics engine.

At block 212, the items that are unavailable in the home inventory database are determined for the recommended recipe. Once a recipe is generated, the core analytics engine may determine the optimal stock that need to be ordered while determining the items unavailable in the home inventory data 132 for the recommended recipe. The determination is based on learning one or more of a frequency of purchase of an item, consumption pattern of the item, and the expiry date of the item. Upon determination, the user may be notified to enable the user place an order requesting for delivery of goods or items from the service provider. This may save a substantial amount of time for the user, as the user may no longer have to keep a manual track of stock of each item in the home inventory.

Although implementations for methods and systems for diet management, personalized to the user, based on health information and home inventory, are described, it is to be understood that the present subject matter is not necessarily limited to the specific features or methods described. Rather, the specific features and methods are disclosed as implementations for diet management, personalized to the user, based on health information and the home inventory.

We claim:

1. A method to manage home inventory based on health targets of a user, the method comprising:
    obtaining, by the processor, at least one health target for the user, wherein the at least one target is related to at least one health parameter from among a plurality of health parameters;
    querying, by the processor a recipe recommender data to recommend at least one recipe from among a plurality of recipes based on the at least one health target;
    ascertaining, by the processor, availability of one or more items to be used in the at least one recipe in a home inventory of the user, wherein the availability is ascertained based on an available stock and an expiry date, wherein the available stock of each item from among the one or more items is determined periodically, by using a core analytics engine, the core analytics engine communicating, via an Internet, with a combination of a plurality of Radio Frequency Identification Devices (RFIDs), sensors and computing devices to determine the available stock of each item in the home inventory, and wherein the periodic determination of the available stock of each item for obtaining optimal stock of each item is based on learning of at least one of a frequency of purchase, a consumption pattern and the expiry date for each item; and
    dynamically generating, by the processor, at least one of a shopping list, coupons, alerts, preferences, burn rate and spend analysis, favorite shopping lists and discounts.

2. The method as claimed in claim 1, wherein the at least one health target is obtained based on comparing the health inputs associated with the at least one health parameter to pre-defined values corresponding to the same health parameter.

3. The method as claimed in claim 1, wherein the home inventory data comprises inventory inputs corresponding to at least one of a item name, quantity, location of purchase, price, and expiry date, for each of the plurality of items.

4. The method as claimed in claim 1, comprises notifying, by the processor, the one or more items unavailable in the home inventory data to enable the user place an order for the unavailable items.

5. An inventory management system to manage home inventory, the inventory management system comprising:
    a processor;
    a health monitoring module coupled to the processor, to obtain at least one health target for the user, wherein the at least one target is related to at least one health parameter from among a plurality of health parameters;
    a recipe recommender module coupled to the processor to query a recipe recommender data to recommend at least one recipe from among a plurality of recipes based on the at least one health target; and
    a consumption monitoring module coupled to the processor to ascertain the availability of one or more items to be used in the at least one recipe in a home inventory of the user, wherein the availability is ascertained based on an available stock and an expiry date, wherein the available stock of each item from among the one or more items is determined periodically, by using a core analytics engine, wherein the core analytics engine communicates, via an Internet, with a combination of a plurality of Radio Frequency Identification devices (RFIDs), sensors and computing devices to determine the available stock of each item in the home inventory, and wherein the periodic determination of the available stock of each item for obtaining optimal stock of each item is based on learning of at least one of a frequency of purchase, a consumption pattern and the expiry date for each item; and
    a smart notification module coupled to the processor that dynamically generates at least one of a shopping list, coupons, alerts, preferences, burn rate and spend analysis, favorite shopping lists and discounts.

6. The inventory management system as claimed in claim 5, comprises an inventory management module coupled to the processor to obtain inventory inputs corresponding to a plurality of purchase parameters, wherein the plurality of purchase parameters comprise one or more of a item name, quantity, location of purchase, price, and expiry date, for each of item from a plurality of items.

7. The inventory management system as claimed in claim 5, wherein the health monitoring module further aggregates the health inputs associated with the at least one health parameter by communicating with at least one of a medical device, and online health portals, over a network by leveraging Internet of Things (IoT).

8. The inventory management system as claimed in claim 5, wherein the health monitoring module determines the at least one health target based on comparing the inputs associated with the at least one health parameter to pre-defined values corresponding to the same health parameter.

9. A non-transitory computer readable medium having a set of computer readable instructions that, when executed, cause a computing system to:
    obtain at least one health target for the user, wherein the at least one target is related to at least one health parameter from among a plurality of health parameters;

query a recipe recommender data to recommend at least one recipe from among a plurality of recipes based on the at least one health target;

ascertain availability of one or more items to be used in the at least one recipe in a home inventory of the user, wherein the availability is ascertained based on an available stock and an expiry date, wherein the available stock of each item from among the one or more items is determined periodically, by using a core analytics engine, the core analytics engine communicates, via an Internet, with a combination of a plurality of Radio Frequency Identification devices (RFIDs), sensors and computing devices to determine the available stock of each item in the home inventory, and wherein the periodic determination of the available stock of each item for obtaining optimal stock of each item is based on learning of at least one of a frequency of purchase, a consumption pattern and the expiry date for each item; and dynamically generate at least one of a shopping list, coupons, alerts, preferences, burn rate and spend analysis, favorite shopping lists and discounts.

* * * * *